United States Patent [19]
Hirai et al.

[11] Patent Number: 5,885,959
[45] Date of Patent: Mar. 23, 1999

[54] CYCLIC PEPTIDE COMPOUNDS AND THEIR PRODUCTION PROCESS

[75] Inventors: Hideo Hirai, Kobe; Nakao Kojima, Nagoya; Hiroyuki Nishida, Handa; Toshiyuki Saito, Toyota; Nobuji Yoshikawa, Anjo, all of Japan

[73] Assignee: Pfizer Inc., New York, N.Y.

[21] Appl. No.: 999,627

[22] Filed: Dec. 3, 1997

[30] Foreign Application Priority Data

Dec. 4, 1996 [WO] WIPO .................. PCT/IB96/01352

[51] Int. Cl.⁶ .......................... A61K 38/12; C07K 5/00; C07K 7/00; C07K 16/00
[52] U.S. Cl. .................. 514/11; 514/9; 530/317
[58] Field of Search ................ 530/317; 514/11, 514/9

[56] References Cited

FOREIGN PATENT DOCUMENTS 0852232  7/1998  European Pat. Off. .

*Primary Examiner*—Cecilia J. Tsang
*Assistant Examiner*—S. G. Marshall
*Attorney, Agent, or Firm*—Peter C. Richardson; Gregg C. Benson; Carl J. Goddard

[57] ABSTRACT

This invention provides processes for producing novel cyclic peptide compounds, which comprise cultivating *Ctenomyces serratus* FERM BP-5731 and then isolating the cyclic peptide compounds from the fermentation broth. The compounds produced by these processes include a cyclic peptide compound of the following formula (I):

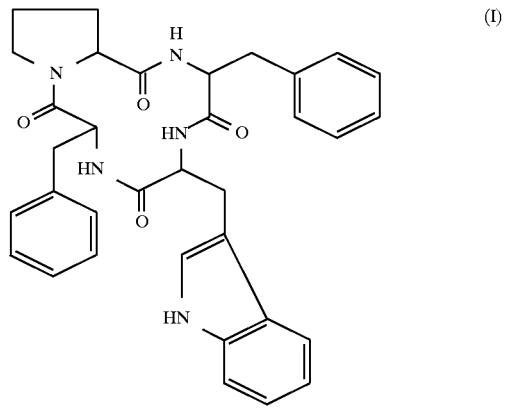

The present invention also relates to a pharmaceutical composition comprising the same, which is useful in the treatment of severe pain, detoxication of narcotics dependency or acute narcotics intoxication or the like.

4 Claims, 4 Drawing Sheets

CYCLIC PEPTIDE COMPOUNDS AND THEIR PRODUCTION PROCESS

This application claims priority from international application PCT/IB96/01352 which was filed internationally on Dec. 4, 1996.

TECHNICAL FIELD

This invention relates to novel cyclic peptide compounds, and particularly to the novel cyclic peptide compounds produced by fermentation of a fungus *Ctenomyces serratus* ATCC 15502, which has been deposited as FERM BP-5731. This invention also relates to a process for producing the cyclic peptide compounds and a pharmaceutical composition comprising the same, which is useful in the treatment of severe pain, narcotics dependency, acute narcotics intoxication or the like in a mammmalial subject especially humans.

BACKGROUND ART

Drugs with opioid receptor binding activity are therapeutically useful for pain and detoxication, and morphine and naloxone are widely used as analgesic and antidote, respectively. But morphine has unwanted side effects such as drug dependency or respiratory depression, and its usage is strictly limited. There is a clear medical need for more efficacious drugs with less side effects. Considerable pharmacological and biochemical studies have suggested that there are at least three major classes of opioid receptors designated $\mu$, $\delta$ and $\kappa$. While morphine has a binding activity for $\mu$ receptor, drugs with binding activity for $\delta$ or $\kappa$ receptors may be more efficacious and have less side effects.

The object of the present invention is to provide novel cyclic peptide compounds having an excellent opioid receptor binding activity and a pharmaceutical composition comprising the same. Another object of the present invention is to provide processes for producing the novel cyclic peptide compounds.

BRIEF DISCLOSURE OF THE INVENTION

Accordingly, the present invention provides the cyclic peptide compounds, CJ-15,208, CJ-15,208-1, CJ-15,208-2 and CJ-15,208-3, wherein (a) said CJ-15,208 has the following chemical formula (I):

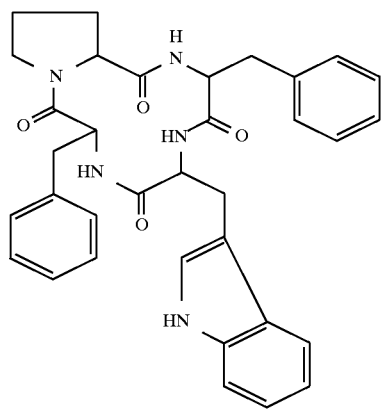

(b) said CJ-15,208-1 has the characteristic FAB mass spectrum with m/z 617 (M+H)$^+$, the UV spectrum with UV max at 210 and 280 nm, the $^1$H NMR spectrum shown in FIG. 2, and a retention time of 12.1 min on HPLC using a YMC Pack ODS column (6.0×150 mm) and eluting with methanol-water (60:40) at a flow rate of 0.8 ml/min at 42° C.;

(c) said CJ-15,208-2 has the characteristic FAB mass spectrum with m/z 678 (M+H)$^+$; the UV spectrum with UV max at 210 and 280 nm; the $^1$H NMR spectrum shown in FIG. 3; and a retention time of 14.8 min on HPLC using a YMC Pack ODS column (6.0×150 mm) and eluting with methanol-water (60:40) at a flow rate of 0.8 ml/min at 42° C.; and (d) said CJ-15,208-3 has the characteristic FAB mass spectrum with m/z 539 (M+H)$^+$; the UV spectrum with UV max at 210; the $^1$H NMR spectrum shown in FIG. 4; and a retention time of 17.8 min on HPLC using a YMC Pack ODS column (6.0×150 mm) and eluting with methanol-water (60:40) at a flow rate of 0.8 ml/min at 42° C.

Further, the present invention provides a process for producing the cyclic peptide compounds, which comprises cultivating a microorganism *Ctenomyces serratus* FERM BP-5731, or a mutant or recombinant form thereof, and then isolating cyclic peptide compounds from the fermentation broth.

Also, the present invention provides a pharmaceutical composition for use in the treatment of severe pain, or detoxication for narcotics dependency or acute narcotics intoxication, which comprises the cyclic peptide compounds and a pharmaceutically acceptable carrier.

Also, the present invention provides a method for the treatment of severe pain, or detoxication for narcotics dependency or acute narcotics intoxication of a subject in need of such treatment, which comprises administering to said subject an antinociception or detoxication amount of the cyclic peptide compounds and a pharmaceutically acceptable carrier.

DETAILED DESCRIPTION OF THE INVENTION

Figure 1:
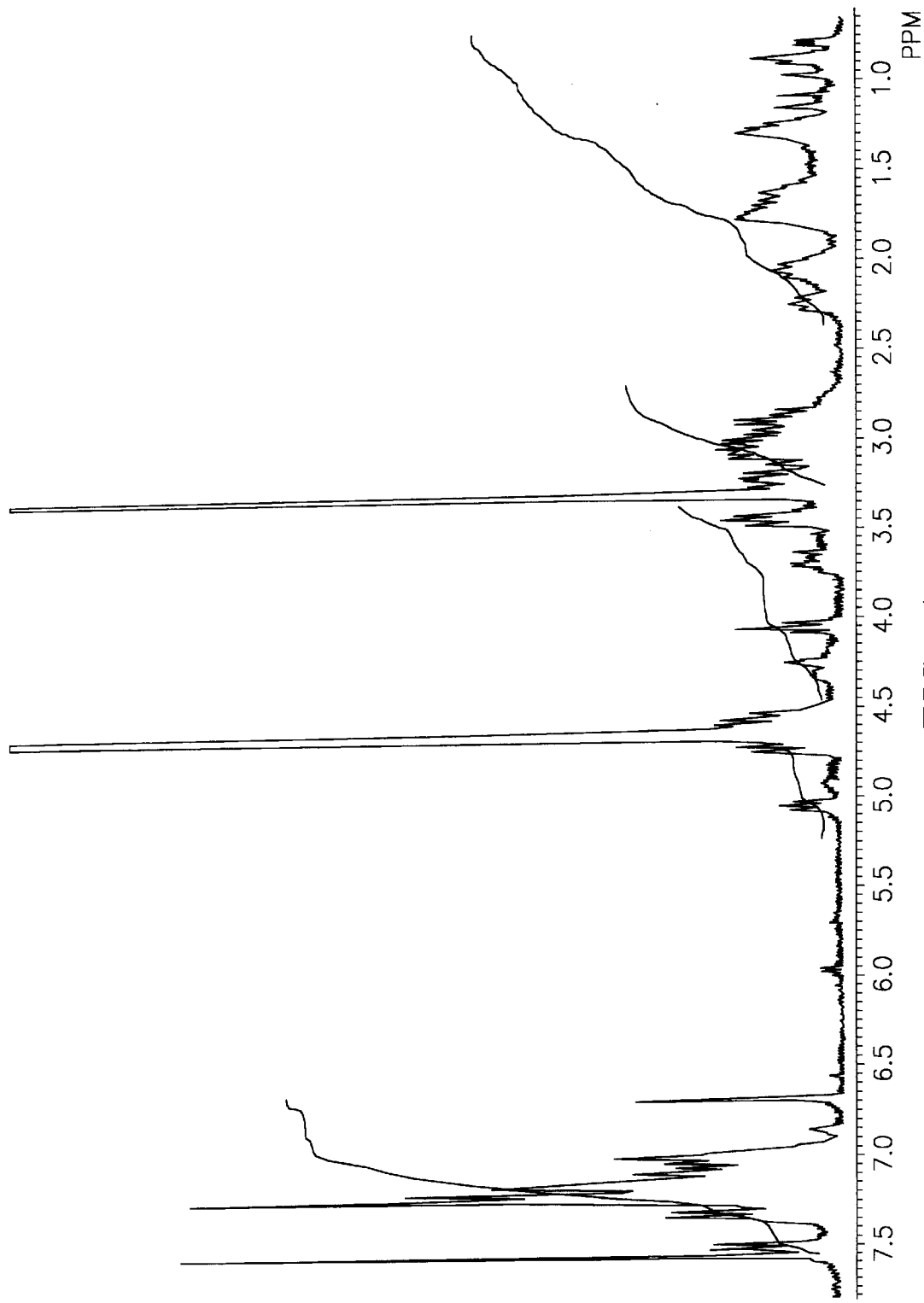
FIG. 1 is the $^1$H NMR spectrum of the compound of CJ-15,208.

The microorganism used in this invention is a strain of *Ctenomyces serratus* ATCC 15502 which was obtained from the American Type Culture Collection (ATCC). It was deposited under the accession number FERM BP-5731 to National Institute of Bioscience and Human-Technology, Agency of Industrial Science and Technology (located at 1-3 Higashi 1-chome, Tsukuba, Ibaraki 305, Japan) under the Budapest Treaty on Oct. 29, 1996. The taxonomical properties of this strain have been reported by Orr, G. F., et al. (*Mycopathol. Mycol. Appl.* 21: 321–333, 1963), describing that this strain is ascomycete *Ctenomyces serratus*.

In this invention, a mutant or recombinant form of FERM BP-5731 having the ability to produce the cyclic peptide compounds can be also used. The mutant or recombinant form may be obtained by spontaneous mutation, artificial mutation with ultraviolet radiation, or treatment with mutagen such as N-methyl-N'-nitro-N-nitrosoguanidine or ethyl methanesulfonate, or a cell technology method such as cell fusion, gene manipulation or the like, according to well-known methods.

According to the present invention, the cyclic peptide compounds may be produced by aerobic fermentation of FERM BP-5731, or a mutant or recombinant form thereof, under conditions similar to those generally employed to produce bioactive compounds by fermentation.

FERM BP-5731, or a mutant or recombinant form thereof, is usually fermented on solid medium with an insoluble material and aqueous nutrient media. The amount of the insoluble material may be in the range of 10 to 50% (w/v). Suitable insoluble materials useful for fermentation include sand, cracked stone, wood chip and whole broken grains, such as wheat bran, oatmeal, cracked corn, millet, etc. In this invention, cultivation of FERM BP-5731 to produce the novel cyclic peptide compounds was preferably carried out using such insoluble materials and aqueous nutrient media at a temperature of 20° to 35° C. for 3 to 20 days. The pH of the medium may be adjusted in the range from 4.0 to 9.0, preferably from 5.0 to 7.5.

Nutrient media useful for fermentation include a source of assimilable carbon such as sugars, starches and glycerol; and a source of organic nitrogen such as casein, enzymatic digest of casein, soybean meal, cotton seed meal, peanut meal, wheat gluten, soy flour, meat extract and fish meal; and a source of growth substances such as mineral salts, sodium chloride and calcium carbonate; and trace elements such as iron, magnesium, copper, zinc, cobalt and manganese.

The cyclic peptide compounds of this invention may be isolated by standard techniques such as extraction and various chromatographic techniques.

The cyclic peptide compounds of this invention were isolated in a substantially pure form from the fermentation mixture, and identified by various spectroscopic techniques such as UV spectrophotometry, NMR and mass spectrometries. According to the analyses, CJ-15,208 is believed to have the following chemical formula:

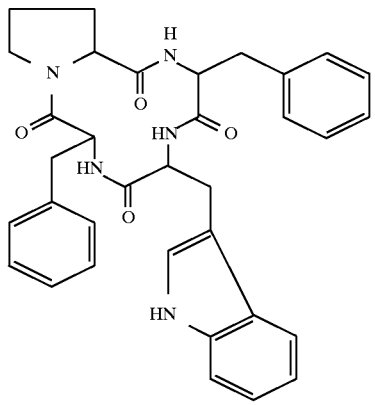

The opioid receptor binding inhibitory activity of the cyclic peptide compounds of this invention was measured by the standard in vitro protocol described below:

Preparation of Guinea pig brain membrane fraction

The brains obtained from fresh Guinea pig or local supplier were rinsed in ice-cold PBS and briefly homogenized in buffer A containing 50 mM HEPES-50 mM Tris-HCl (pH 7.5), 0.24M sucrose, 5 mM MgCl$_2$, 2 mM EGTA, 100 µM PMSF and 50 µM leupeptin. The homogenate was centrifuged at 900×g for 10 min at 4° C. The supernatant was recentrifuged at 80,000×g for 30 min at 4° C. After centrifugation, the supernatant was removed and the pellet (membrane fraction) was suspended in buffer A. The membrane fractions were stored at −80° C. until use. Under this condition, ligand-binding activity was stable for at least 5 months.

Opioid Receptor Binding Assay

Assay was performed in 96-well microtiter plates containing a 200-µl reaction mixture per well which consists of 40 mM HEPES-40 mM Tris-HCl (pH 7.5), 0.192M sucrose, 4 mM MgCl$_2$, 1.6 mM EGTA, 80 µM PMSF and 40 µM leupeptin, Guinea pig brain membrane fraction, and 1 nM [$^3$H] CI-977, 1 nM [D-ala$^2$, N-methyl-phe$^4$, glycol$^5$] [tyrosyl-3,5-$^3$H] enkephalin (DAMGO), or 1 nM [D-penicillamine$^2$, D-penicillamine$^5$][tyrosyl-2,6-$^3$H(N)] enkephalin (DPDPE). After incubation at room temperature with shaking for 30 min, reaction was terminated by harvesting reaction mixtures onto polyetheleneimine-soaked glassfilters. After drying, radioactivity was measured by a scintillation counter. Binding inhibitory activity is calculated by the following formula:

$$\text{Inhibition (\%)} = \left(1 - \frac{[DPM \text{ Sample} - DPM \text{ Blank}]}{[DPM \text{ Control} - DPM \text{ Blank}]}\right) \times 100$$

The cyclic peptide compounds of this invention showed an inhibition rate in the range from 50 ng/ml to 1 µg/ml.

The cyclic peptide compounds of this invention are useful as an analgesic agent, antidotal agent or the like. The analgesic and antidotal activities can be demonstrated by the following methods.

Analgesic Activity Assay

The analgesic activity of the cyclic peptide compouds of this invention can be demonstrated by the Formalin Test as described by Wheeler-Aceto, H. et al. in *Psychopharmacology*, 104: 35–44, 1991. In this testing, male SD rats (80–100 g) are injected s.c. with a test compound dissolved in 0.1% methyl cellulose saline or vehicle. After 30 min., 50 µl of a 2% formalin are injected into a hind paw. The number of licking the injected paw per observation period is measured 15–30 min. after the injection of formalin and expressed as % inhibition compared to the respective vehicle group.

Detoxication Activity Assay

The detoxication activity of the compounds of this invention can be demonstrated according to the procedure described by Fu-Hsiung Shen, Horace H. Loh and E. Leong Way in *The Journal Of Pharmacology And Experimental Therapeutics*, 175: 427–434, 1970. In this testing, Swiss albino male mice, weighing 20 to 25 g, are rendered dependent to narcotics by repeated injections of narcotics for three weeks at increasing doses. The starting dose is 5 mg/kg s.c. three times daily, and this is increased in 25-mg/kg increments every three days until a final dose of 175 mg/kg is attained. A second group of mice receives the same dosage of narcotics but, in addition, an injection of the cyclic peptide compounds of this invention 15 minutes before the narcotics. The dosage of the cyclic peptide compounds of this invention is adjusted so that the dose ratio of the cyclic peptide compounds of this invention/narcotics is 1:12.5. A third group of animals receives saline or the cyclic peptide compounds of this invention three times daily. The percentage of animals that leap off a circular platform within 15 minutes after administration is determined.

The detoxication activity of the compounds of this invention against acute narcotics intoxication, can be demonstrated according to the procedure described by J. E. Eckenhoff et. al. in *Am. J. Med. Sci.,* 228 (5), 546, 1954.

Administration

The cyclic peptide compounds, CJ-15,208, CJ-15,208-1, CJ-15,208-2 and CJ-15,208-3, are useful in the treatment of severe pain, detoxication for narcotics dependency or acute narcotics intoxication, or the like. These cyclic peptide compounds may be administered alone or in combination with pharmaceutically acceptable carriers, in either single or multiple doses. Suitable pharmaceutical carriers include inert solid diluents or fillers, sterile aqueous solution and various organic solvents. The pharmaceutical compositions formed by combining these cyclic peptide compounds and the pharmaceutically acceptable carriers are then readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredients therein may be combined with various sweetening or flavoring agents, coloring matter or dyes and, if desired, emulsifying or suspending agents, together with diluents such as water, ethanol, propylene glycol, glycerol and combinations thereof.

For parenteral administration, solutions of the cyclic peptide compounds of this invention in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, the sterile aqueous media employed are all readily available by standard techniques known to those skilled in the art.

Additionally, the cyclic peptide compounds of this invention may be administered topically when treating conditions of the skin and this may be done by way of creams, jellies, gels, pastes, and ointments, in accordance with standard pharmaceutical practice.

In general, a therapeutically effective daily dose for the active compound will range from 0.01 to 100 mg/kg, generally from about 1 to about 5 mg/kg, body weight of the subject to be treated for severe pain, or detoxication for narcotics dependency or acute narcotics intoxication from 0.2 to 100 mg/kg. As is generally known, the effective dosage for the active compound depends on the intended route of administration and other factors such as age and weight of the patient, as generally known to a physician. The dosage also depends on the illness to be treated.

EXAMPLES

The present invention is illustrated by the following examples. However, it should be understood that the invention is not limited to the specific details of these examples. Spectral and physico-chemical data were obtained by the following instruments: IR, Shimadzu IR-470; UV, JASCO Ubest-30; Optical rotations, JASCO DIP-370 with a 5 cm cell; NMR, JEOL JNM-GX270 equipped with a LSI-11/73 host computer, TH-5 tunable probe and version 1.6 software; and FAB-MS, JEOL JMS-700. All NMR spectra were measured in acetone-$d_6$ containing a small amount of DMSO-$d_6$ unless otherwise indicated and peak positions are expressed in parts per million (ppm) based on the reference of acetone peak at 2.0 ppm for $^1$H NMR and 30.3 ppm for $^{13}$C NMR. The peak shapes are denoted as follows: s (singlet), d (doublet), t (triplet), q (quartet), m (multiplet) and br (broad). All FAB-MS spectra were measured using glycerol-matrix.

Example One

Fermentation of *Ctenomyces serratus* (FERM BP-5731)

One hundred ml of Medium-1 (potato dextrose broth 2.4%, yeast extract 0.5% and agar 0.1%) in a 500-ml flask was inoculated with a vegetative cell suspension from a slant culture of FERM BP-5731. The flask was shaken at 26° C. for 4 days on a rotary shaker with 7-cm throw at 210 rpm, to obtain a first seed culture.

Five 500-ml flasks containing Medium-1 (100 ml) were each inoculated with 5 ml of the first seed culture. These flasks were shaken at the same condition as the first seed culture. The second seed culture was used to inoculate one hundred 500-ml flasks containing Medium-2 (glucose 1%, glycerol 3%, peptone 0.5%, NaCl 0.2% and agar 0.1%, pH 7.0) and 20 g of wheat bran. Incubation was carried out at 26° C. for 10 days.

Extraction and Isolation

The fermentation broth thus obtained was extracted with 10 l of 70% aqueous ethanol. The filtrate was concentrated to aqueous solution (2 l) and extracted twice with 2 l of ethyl acetate. The extract was dried over anhydrous $Na_2SO_4$ and evaporated to afford an oily residue. The residue (7.2 g) was applied to a Sephadex LH-20 column (25×500 mm, Pharmacia trademark) and eluted with methanol. Active fractions (1.3 g) were applied to a YMC-Pack ODS AM-343 column (20×250 mm, Yamamura trademark) and eluted with methanol-water (60:40) at a flow rate of 6 ml/min. Detection was made by UV absorbance at 220 nm. The eluted peaks showing activity were collected to yield the cyclic peptide compounds, CJ-15,208 (5.8 mg), CJ-15,208-1 (11.6 mg), CJ-15,208-2 (4.7 mg) and CJ-15,208-3 (4.9 mg).

HPLC Analysis

Analytical HPLC of samples containing the cyclic peptide compounds of CJ-15,208, CJ-15,208-1, CJ-15,208-2 and CJ-15,208-3 was performed using a YMC-Pack ODS AM-312 column (6.0×150 mm, Yamamura trademark) and eluted with methanol-water (60:40) at a flow rate of 0.8 ml/min. The retention times of the cyclic peptide compounds, CJ-15,208, CJ-15,208-1, CJ-15,208-2 and CJ-15,208-3 were 12.6, 12.1, 14.8 and 17.8 min, respectively.

Characterization

The physico-chemical properties of the cyclic peptide compounds obtained were as follows:

CJ-15,208: White amorphous powder; molecular formula $C_{34}H_{35}N_5O_4$; LRFAB-MS m/z 576 (M−H)$^-$; HRFAB-MS (m/z) 576.2658 (calcd. for $C_{34}H_{34}N_5O_4$, 576.2613); $[\alpha]_D^{24}$ −64.0° (c 0.05, DMSO); UV λmax (MeOH) nm 210, 280; IR υmax (KBr) cm$^{-1}$ 3520, 3290, 1694, 1601, 1516, 1451, 1230, 1105, 741, 696; $^1$H NMR shown in FIG. 1; $^{13}$C NMR δ 175.15 (s), 174.02 (s), 174.02 (s), 170.59 (s), 139.35 (s), 138.19 (s), 137.65 (s), 130.83 (d), 130.83 (d), 130.25 (d), 130.25 (d), 129.23 (d), 129.23 (d), 129.10 (d), 129.10 (d), 128.80 (s), 127.45 (d), 127.45 (d), 124.32 (d), 121.93 (d), 119.70 (d), 119.44 (d), 112.36 (d), 112.18 (s), 60.97 (d), 59.82 (d), 59.46 (d), 58.20 (d), 48.86 (t), 38.62 (t), 36.92 (t), 33.63 (t), 28.24 (t), 21.52 (t).

CJ-15,208-1: White amorphous powder; $^1$H NMR shown in FIG. 2; LRFAB-MS m/z 617 (M+H)$^+$; UV λmax (MeOH) nm 220, 280.

CJ-15,208-2: White amorphous powder; $^1$H NMR shown in FIG. 3; LRFAB-MS m/z 578 (M+H)$^+$; UV λmax (MeOH) nm 210, 280.

CJ-15,208-3: White amorphous powder; $^1$H NMR shown in FIG. 4; LRFAB-MS m/z 539 (M+H)$^+$; UV λmax (MeOH) nm 210.

We claim:

1. A cyclic peptide compound selected from the group consisting of CJ-15,208; CJ-15,208-1; CJ-15,208-2 and CJ-15,208-3, wherein (a) said CJ-15,208 has the following chemical formula (I):

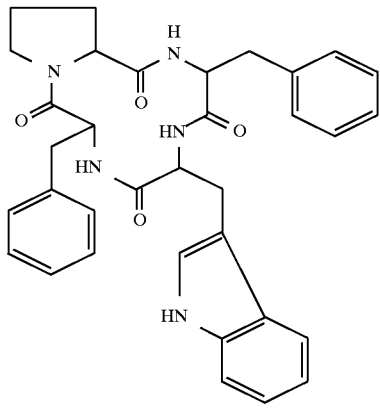

(I)

Figure 2:
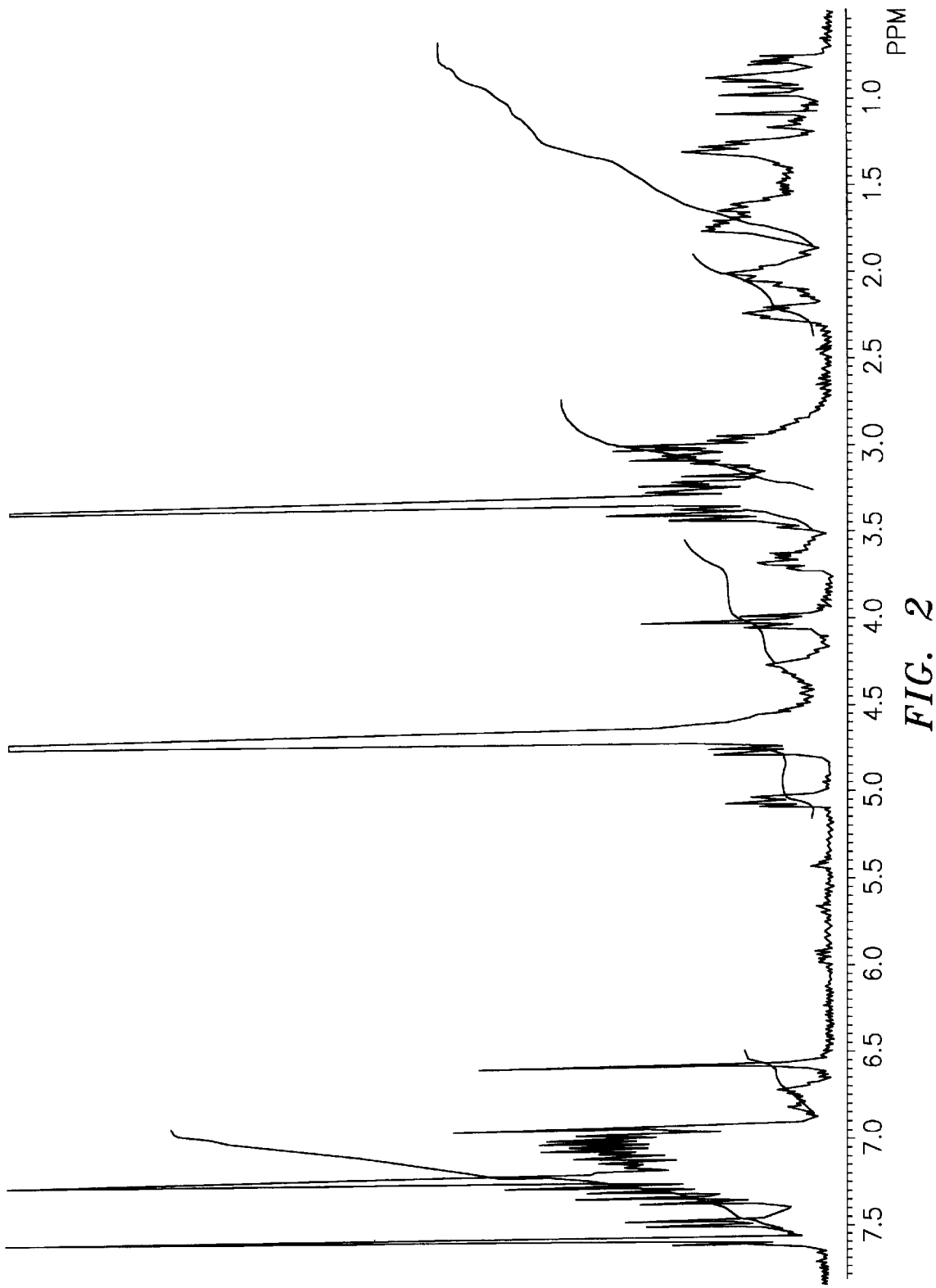
FIG. 2 is the $^1$H NMR spectrum of the compound of CJ-15,208-1.
Figure 3:
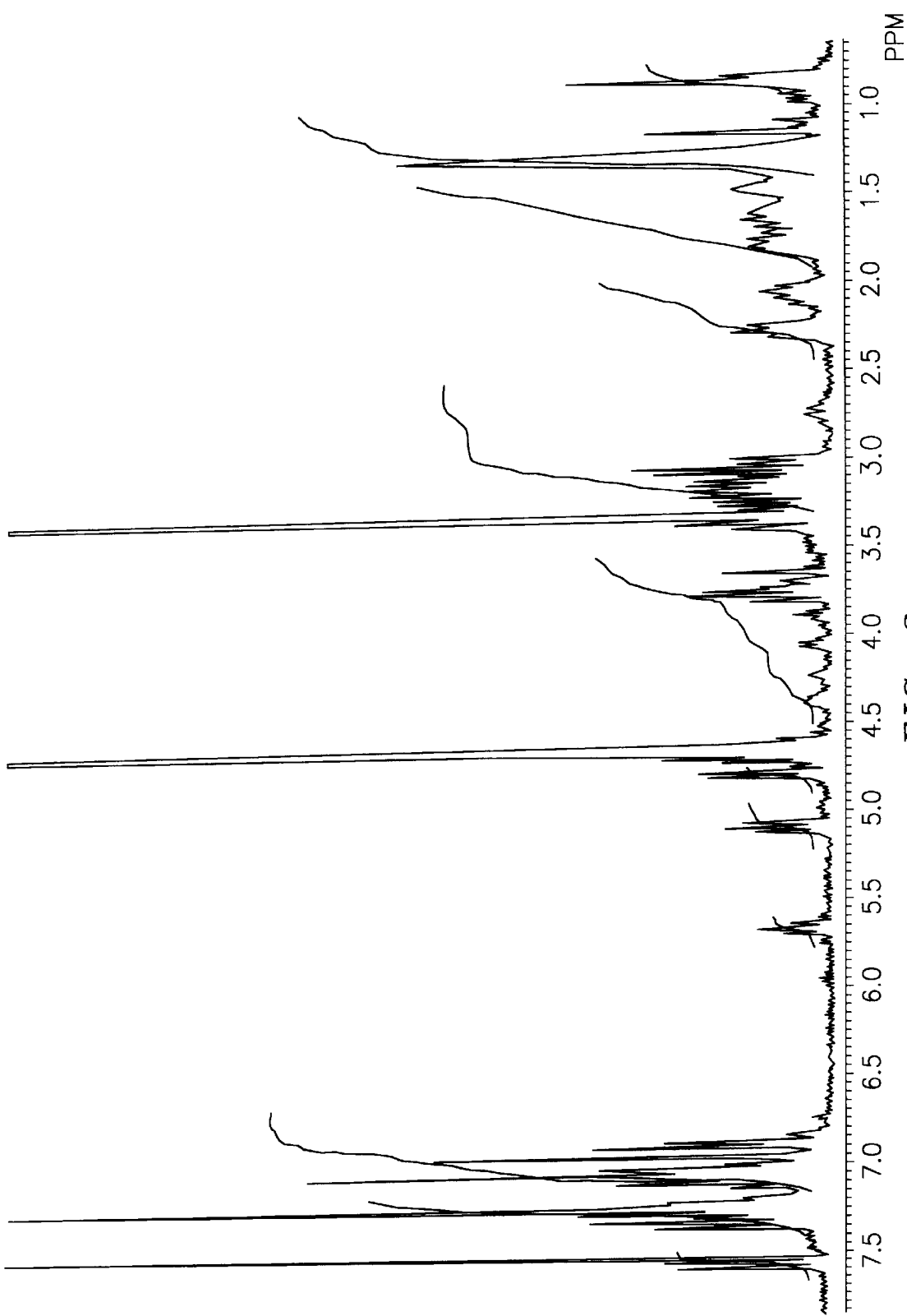
FIG. 3 is the $^1$H NMR spectrum of the compound of CJ-15,208-2.
Figure 4:
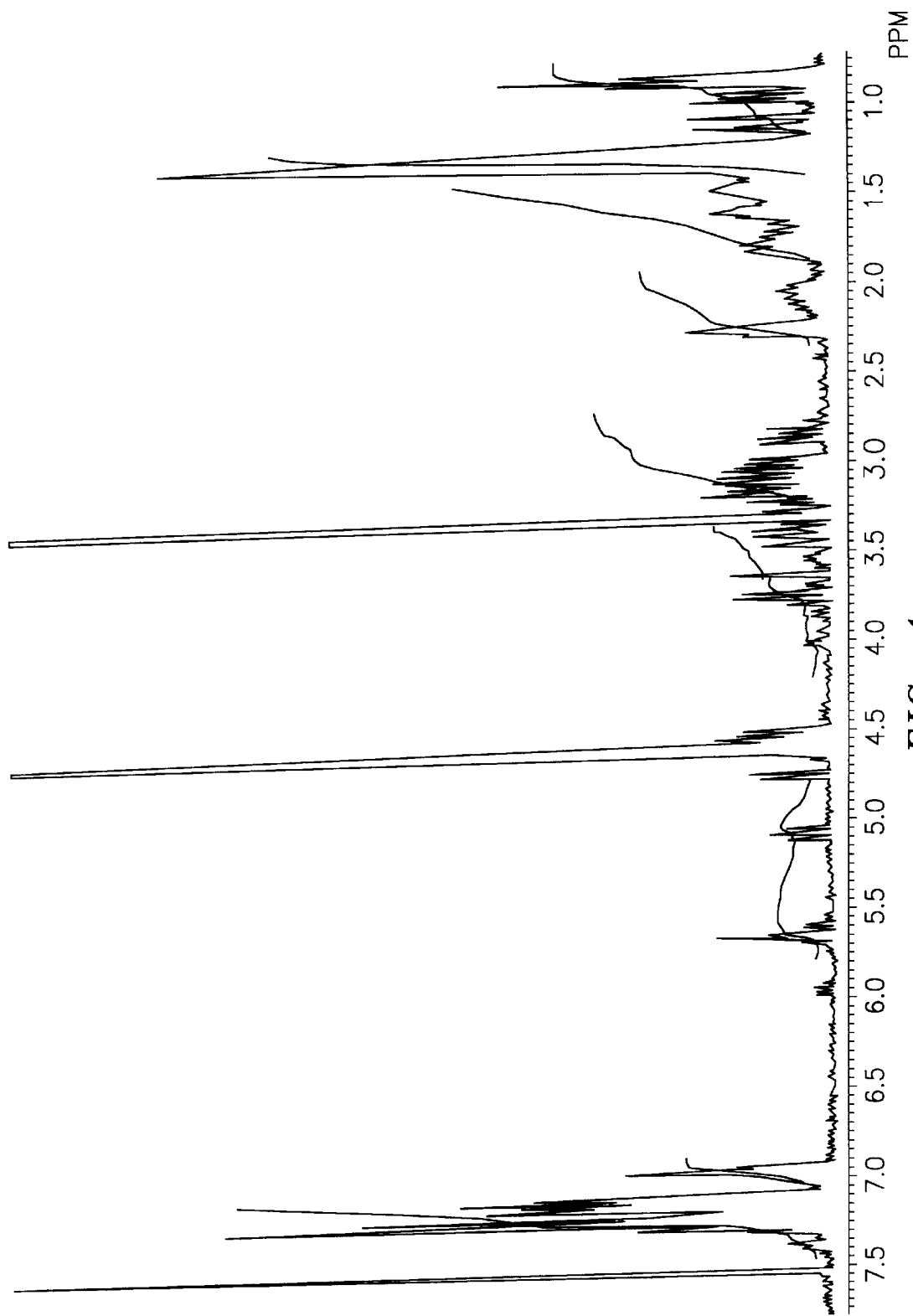
FIG. 4 is the $^1$H NMR spectrum of the compound of CJ-15,208-3.

(b) said CJ-15,208-1 has the characteristic FAB mass spectrum with m/z 617 (M+H)$^+$, the UV spectrum with UV max at 210 and 280 nm, the $^1$H NMR spectrum shown in FIG. 2, and a retention time of 12.1 min on HPLC using a YMC Pack ODS column (6.0×150 mm) and eluting with methanol-water (60:40) at a flow rate of 0.8 ml/min at 42° C.;

(c) said CJ-15,208-2 has the characteristic FAB mass spectrum with m/z 678 (M+H)$^+$; the UV spectrum with UV max at 210 and 280 nm; the $^1$H NMR spectrum shown in FIG. 3; and a retention time of 14.8 min on HPLC using a YMC Pack ODS column (6.0×150 mm) and eluting with methanol-water (60:40) at a flow rate of 0.8 ml/min at 42° C.; and (d) said CJ-15,208-3 has the characteristic FAB mass spectrum with m/z 539 (M+H)$^+$; the UV spectrum with UV max at 210 nm; the $^1$H NMR spectrum shown in FIG. 4; and a retention time of 17.8 min on HPLC using a YMC Pack ODS column (6.0×150 mm) and eluting with methanol-water (60:40) at a flow rate of 0.8 ml/min at 42° C.

2. A process for producing cyclic peptide compounds according to claim 1, which comprises cultivating a microorganism *Ctenomyces serratus* FERM BP-5731, or a mutant or recombinant form thereof, and then isolating cyclic peptide compounds from the fermentation broth.

3. A pharmaceutical composition for use in the treatment of severe pain, or detoxication for narcotics dependency or acute narcotics intoxication comprising a compound according to claim 1 and a pharmaceutically acceptable carrier.

4. A method for the treatment of severe pain, or detoxication for narcotics dependency or acute narcotics intoxication of a subject in need of such treatment, which comprises administering to said subject an antinociception or detoxication amount of a compound according to claim 1 and a pharmaceutically acceptable carrier.

* * * * *

UNITED STATES PATENT AND TRADEMARK OFFICE
CERTIFICATE OF CORRECTION

PATENT NO. : 5,885,959

DATED : March 23, 1999

INVENTOR(S) : Hideo Hirai, Kobe; Nakao Kojima, Nagoya; Hiroyuki Nishida, Handa; Toshiyuki Saito, Toyota; Nobuji Yoshikawa, Anjo, all of Japan It is certified that error appears in the above-identified patent and that said Letters Patent is hereby corrected as shown below:

Column 2, line 2 "m/z 678" should read --m/z 578--; and
Column 8, line 6 "m/z 678" should read --m/z 578--

Signed and Sealed this

Twenty-third Day of November, 1999

Attest:

Q. TODD DICKINSON

*Attesting Officer*　　*Acting Commissioner of Patents and Trademarks*